(12) United States Patent
Nielsen

(10) Patent No.: US 8,980,905 B2
(45) Date of Patent: Mar. 17, 2015

(54) BENZODIOXOLE OR BENZODIOXEPINE HETEROCYCLIC COMPOUNDS AS PHOSPHODIESTERASE INHIBITORS

(75) Inventor: Simon Feldbæk Nielsen, Herlev (DK)

(73) Assignee: Leo Pharma A/S, Ballerup (DK)

( * ) Notice: Subject to any disclaimer, the term of this patent is extended or adjusted under 35 U.S.C. 154(b) by 0 days.

(21) Appl. No.: 13/806,659

(22) PCT Filed: Jun. 24, 2011

(86) PCT No.: PCT/DK2011/000069
§ 371 (c)(1),
(2), (4) Date: Jan. 29, 2013

(87) PCT Pub. No.: WO2011/160632
PCT Pub. Date: Dec. 29, 2011

(65) Prior Publication Data
US 2013/0123291 A1    May 16, 2013

Related U.S. Application Data

(60) Provisional application No. 61/358,209, filed on Jun. 24, 2010.

(51) Int. Cl.
| | | |
|---|---|---|
| A01N 43/42 | (2006.01) |
| C07D 495/10 | (2006.01) |
| C07D 493/10 | (2006.01) |
| A61K 31/4427 | (2006.01) |
| A61K 31/4433 | (2006.01) |

(52) U.S. Cl.
CPC ............ *C07D 495/10* (2013.01); *C07D 493/10* (2013.01); *A61K 31/4427* (2013.01); *A61K 31/4433* (2013.01)
USPC ............................................. 514/278; 546/15

(58) Field of Classification Search
USPC ............................................. 514/278; 546/15
See application file for complete search history.

(56) References Cited

FOREIGN PATENT DOCUMENTS

WO    WO 2008/104175 A2    9/2008

OTHER PUBLICATIONS

Bäumer et al., "Highly Selective Phosphodiesterase 4 Inhibitors for the Treatment of Allergic Skin Diseases and Psoriasis" Inflammation & Allergy—Drug Targets, 2006, vol. 6, pp. 17-26.
Bundschuh et al., "In Vivo Efficacy in Airway Disease Models of Roflumilast, a Novel Orally Active PDE4 Inhibitor", The Journal of Pharmacology and Experimental Therapeutics, vol. 297, No. 1, Jan. 1, 2001, pp. 280-290.
Holden et al., "Monocyte Localization of Elevated cAMP Phosphodiesterase Activity in Atopic Dermatitis", The Society for Investigative Dermatology, Inc., vol. 87, No. 3, 1986, pp. 372-376.
Houslay et al., "Phosphodiesterase-4 as a therapeutic target", DDT, vol. 10, No. 22, Nov. 2005, pp. 1503-1519.
Huang et al., "Phosphodiesterase 4 Inhibitors for the Treatment of Asthma and COPD", Current Medicinal Chemistry, 2006, vol. 13, pp. 3253-3262.
International Search Report mailed on Aug. 19, 2011, issued in PCT/DK2011/000069.
Kroegel et al., "Phosphodiesterase-4 inhibitors as a novel approach for the treatment of respiratory disease: cilomilast", Expert Opin. Investig. Drugs, (2007), vol. 16, No. 1, pp. 109-124.
Leroux et al., "[alpha]-Fluorinated Ethers, Thioethers, and Amines: Anomerically Biased Species", Chem. Rev. Mar. 1, 2005, vol. 105, No. 3, pp. 827-856.
Lipworth, "Phosphodiesterase-4 inhibitors for asthma and chronic obstructive pulmonary disease", Lancet, Jan. 8, 2005; vol. 365: 167-175.
Park et al., "Metabolism of Fluorine-Containing Drugs", Annu. Rev. Pharmacol. Toxicol., Apr. 2001, vol. 41, No. 1, pp. 443-470.
Smith et al., "Selective phosphodiesterase 4 inhibitors in the treatment of allergy and inflammation", Current Opinion in investigational Drugs, 2005, vol. 6, No. 11, pp. 1136-1141.
Written Opinion of the International Searching Authority mailed on Aug. 19, 2011, issued in PCT/DK2011/000069.

*Primary Examiner* — Wu-Cheng Winston Shen
*Assistant Examiner* — Jean Cornet
(74) *Attorney, Agent, or Firm* — Birch, Stewart, Kolasch & Birch, LLP

(57) ABSTRACT

Compounds of the general formula (I) wherein each of m and n is independently 0 or 1; $R_1$ and $R_2$, together with the carbon atom to which they are attached, form a heterocyclic ring comprising one or two heteroatoms selected from oxygen, sulfur, —S(O)— and —S(O)$_2$—; $R^3$ is —CHF$_2$, —CF$_3$, —OCHF$_2$, —OCF$_3$, —SCHF$_2$ or —SCF$_3$; X is a bond, —CH$_2$—, or —NH—; A is aryl, cycloalkyl, cycloalkenyl, arylalkyl, heteroaryl, heteroarylalkyl, heterocycloalkyl or heterocycloalkenyl, optionally substituted with one or more, same or different substituents selected from $R_4$; and $R_4$ is hydrogen, amino, thioxo, alkyl, haloalkyl, hydroxyalkyl, alkoxy, haloalkoxy, halogen, oxo, thia, or hydroxy; or pharmaceutically acceptable salts, hydrates or solvates thereof, have been found to exhibit PDE4 inhibiting activity, and may therefore be useful in the treatment of inflammatory diseases and disorders.

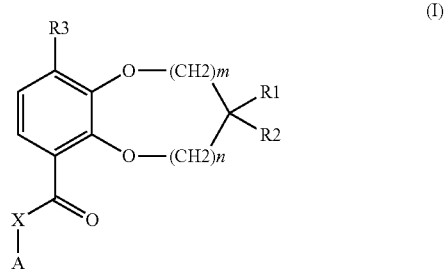

35 Claims, No Drawings

BENZODIOXOLE OR BENZODIOXEPINE HETEROCYCLIC COMPOUNDS AS PHOSPHODIESTERASE INHIBITORS

CROSS REFERENCE TO RELATED APPLICATIONS

This application is the National Phase of PCT/DK2011/000069 filed on Jun. 24, 2011, which claims priority under 35 U.S.C. 119(e) to U.S. Provisional Application No. 61/358,209 filed on Jun. 24, 2010, all of which are hereby expressly incorporated by reference into the present application.

FIELD OF INVENTION

The present invention relates to novel compounds with phosphodiesterase inhibitory activity, as well as to their use as therapeutic agents in the treatment of inflammatory diseases and conditions.

BACKGROUND OF THE INVENTION

Phosphodiesterases are enzymes that catalyse the hydrolysis of cyclic AMP and/or cyclic GMP in cells to 5-AMP and 5-GMP, respectively, and as such they are critical to cellular regulation of cAMP or cGMP levels. Of the 11 phosphodiesterases identified so far, phosphodiesterase (PDE) 4, PDE7 and PDE8 are selective for cAMP. PDE4 is the most important modulator of cAMP expressed in immune and inflammatory cells such as neutrophils, macrophages and T-lymphocytes (Z. Huang and J. A. Mancini, *Current Med. Chem.* 13, 2006, pp. 3253-3262). As cAMP is a key second messenger in the modulation of inflammatory responses, PDE4 has been found to regulate inflammatory responses of inflammatory cells by modulating proinflammatory cytokines such as TNFα, IL-2, IFN-γ, GM-CSF and LTB4. Inhibition of PDE4 has therefore become an attractive target for the therapy of inflammatory diseases such as asthma, chronic obstructive pulmonary disease (COPD), rheumatoid arthritis, atopic dermatitis, Crohn's disease etc. (M. D. Houslay et al., *Drug Discovery Today* 10 (22), 2005, pp. 1503-1519). As atopic dermatitis (AD) patients have increased PDE-activity, PDE4-inhibition would also appear to be a viable treatment of AD (Journal of Investigative Dermatology (1986), 87(3), 372-6).

The PDE4 gene family consists at least of four genes, A, B, C and D, which have a high degree of homology (V. Boswell Smith and D. Spina, *Curr. Opinion Investig. Drugs* 6(11), 2006, pp. 1136-1141). The four PDE4 isoforms are differentially expressed in different tissues and cell types. Thus, PDE4B is predominantly expressed in monocytes and neutrophils, but not in cortex and epithelial cells, while PDE4D is expressed in lung, cortex, cerebellum and T-cells (C. Kroegel and M. Foerster, *Exp. Opinion Investig. Drugs* 16(1), 2007, pp. 109-124). It has been speculated that inhibition of PDE4D in the brain is associated with the adverse effects found when administering PDE4 inhibitors clinically, primarily nausea and emesis, whereas inhibition of PDE4B is associated with anti-inflammatory effects (B. Lipworth, *Lancet* 365, 2005, pp. 167-175). However, the PDE inhibitors developed so far are not believed to be specific for any of the four PDE4 isoforms.

Numerous PDE4 inhibitors have been studied for their therapeutic effect on inflammatory diseases, primarily asthma, inflammatory bowel disease and COPD. The first of these, theophylline, is a weak, non-selective phosphodiesterase inhibitor used in the treatment of respiratory diseases such as asthma and COPD. Treatment with theophylline may, however, give rise to both mild and severe adverse effects, e.g. arrhythmia and convulsions, restricting the clinical utility of theophylline (Kroegel and Foerster, supra). As phosphodiesterase has remained an attractive target for anti-inflammatory therapy, several other, more selective PDE4 inhibitors have been developed and investigated in a clinical setting. The clinical development of many of the first-generation PDE4 inhibitors such as rolipram was discontinued due to dose-limiting side effects, primarily nausea and emesis. Second-generation PDE4 inhibitors with apparently less pronounced adverse effects are currently in clinical trials (Houslay, supra).

Recently developed PDE-4 inhibitors are for example disclosed in EP 0771794 and EP 0943613. WO 96/31476 discloses structurally different 4-substituted-3,5-dichloropyridines which are inhibitors of cyclic AMP phosphodiesterase.

WO 2008/104175 discloses 4-substituted 3,5-dichloropyridine compounds wherein the substituent comprises a spiro benzodioxole or benzodioxepine heterocyclic ring system. These compounds are disclosed to be PDE4 inhibitors, and are intended for topical administration as they are subjected to degradation when administered orally.

An overview of preclinical and clinical trials with selective PDE4 inhibitors, including such inhibitors aimed for the treatment of atopic dermatitis and psoriasis, was recently given in Inflammation & Allergy: Drug Targets, 2007, 6(1), 17-26.

There is a continued need for developing novel PDE4 inhibitors which have a more favourable therapeutic window, i.e. fewer adverse effects upon oral administration, while retaining their therapeutic anti-inflammatory effect.

SUMMARY OF THE INVENTION

The inventors have surprisingly found that the compounds of the present invention exhibit PDE4 inhibitory activity upon oral administration and may be useful as therapeutic agents for systemic treatment of inflammatory allergic diseases such as bronchial asthma, COPD, allergic rhinitis, and nephritis; autoimmune diseases such as rheumatoid arthritis, multiple sclerosis, Crohn's disease, and systemic lupus erythematosus; diseases of the central nervous system such as depression, amnesia, and dementia; organopathy associated with ischemic reflux caused by cardiac failure, shock, and cerebrovascular diseases, and the like; insulin-resistant diabetes; wounds; and other diseases where inflammation plays a part in the etiology or progression of the disease.

Compounds of the present invention may also be beneficial in preventing, treating or ameliorating a variety of diseases, such as dermal diseases or conditions, such as proliferative and inflammatory skin disorders and in particular psoriasis, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

Accordingly, the present invention relates to a compound of general formula I

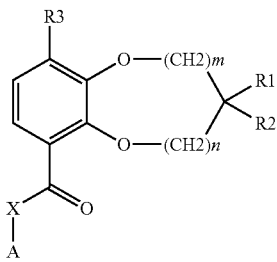

wherein
each of m and n is independently 0 or 1;
R$_1$ and R$_2$, together with the carbon atom to which they are attached, form a heterocyclic ring comprising one or two heteroatoms selected from oxygen, sulfur, —S(O)— and —S(O)$_2$—;
R$_3$ is —CHF$_2$, —CF$_3$, —OCHF$_2$, —OCF$_3$, —SCHF$_2$ or —SCF$_3$;
X is a bond, —CH$_2$—, or —NH—;
A is aryl, cycloalkyl, cycloalkenyl, arylalkyl, heteroaryl, heteroarylalkyl, heterocycloalkyl or heterocycloalkenyl, optionally substituted with one or more, same or different substituents selected from R$_4$; and
R$_4$ is hydrogen, amino, thioxo, alkyl, haloalkyl, hydroxyalkyl, alkoxy, haloalkoxy, halogen, oxo, thia, or hydroxy;
or a pharmaceutically acceptable salt, hydrate, or solvate thereof.

Compounds of a similar chemical structure are known from WO 2008/104175. These compounds are generally known to be quickly metabolised and inactivated upon systemic/oral administration as the methoxy group (R$_3$=OCH$_3$) is cleaved to a hydroxyl group (R$_3$=OH) as shown in example 15. However, in the compounds of this invention, metabolism of R$_3$ and hence inactivation is substantially reduced. Thus, for instance when A is 3,5-dichloropyridine the compounds of formula IIa are metabolised to the metabolically more stable and active N-oxide (IIb) and when A is 3,5-dichloropyridine-N-oxide the compounds are generally metabolically stable making the compounds suited for systemic, in particular oral, administration—cf. example 15.

In another aspect, the invention relates to compounds of general formula I for use in therapy.

DETAILED DISCLOSURE OF THE INVENTION

Definitions

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-20 carbon atoms, and preferably comprises 1-12, e.g. 1-6, e.g. 1-4, e.g. 1-3, e.g. 1-2 carbon atoms. The term includes alkyl, alkenyl, cycloalkyl, cycloalkenyl, alkynyl and aryl, arylalkyl.

The term "aryl" is intended to indicate a radical of aromatic carbocyclic rings comprising 6-20 carbon atoms, such as 6-14 carbon atoms, preferably 6-10 carbon atoms, in particular 5- or 6-membered rings, optionally fused carbocyclic rings with at least one aromatic ring, such as phenyl, naphthyl, indenyl and indanyl.

The term "heteroaryl" is intended to indicate radicals of heterocyclic aromatic rings comprising 1-6 heteroatoms (selected from O, S and N) and 1-20 carbon atoms, such as 1-5 heteroatoms and 1-10 carbon atoms, such as 1-5 heteroatoms and 1-6 carbon atoms, such as 1-5 heteroatoms and 1-3 carbon atoms, in particular 5- or 6-membered rings with 1-4 heteroatoms selected from O, S and N, or optionally fused bicyclic rings with 1-4 heteroatoms, and wherein at least one ring is aromatic, e.g. pyridyl, quinolyl, isoquinolyl, indolyl, tetrazolyl, thiazolyl, imidazolyl, pyrazolyl, oxazolyl, isoxazolyl, thienyl, pyrazinyl, isothiazolyl, benzimidazolyl and benzofuranyl.

In the present context, the term "alkyl" is intended to indicate the radical obtained when one hydrogen atom is removed from a hydrocarbon. Said alkyl comprises 1-20, preferably 1-12, such as 1-6, such as 1-4 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, pentyl, isopentyl, hexyl and isohexyl.

The term "cycloalkyl" is intended to indicate a saturated cycloalkane radical comprising 3-20 carbon atoms, preferably 3-10 carbon atoms, in particular 3-8 carbon atoms, such as 3-6 carbon atoms, including fused bicyclic rings, e.g. cyclopropyl, cyclobutyl, cyclopentyl, cyclohexyl, or cycloheptyl.

The term "heterocycloalkyl" is intended to indicate a cycloalkane radical as described above, wherein one or more carbon atoms are replaced by heteroatoms, comprising 1-19 carbon atoms, e.g. 2-4 carbon atoms, further comprising 1-6 heteroatoms, preferably 1, 2, or 3 heteroatoms, selected from O, N, or S, which may optionally be oxidised once or twice, e.g. [1,3]dioxole, oxetane, [1,3]dioxolane, [1,3]dioxane, tetrahydrothiopyran, tetrahydrothiopyran-1,1-dioxide, tetrahydrothiopyran-1-oxide, piperidine, tetrahydrothiophene, [1,3]-dithiane, thietane, [1,3]-dithiane-1,3-dioxide, or thietane-1-oxide, or including fused bicyclic rings with 1-4 heteroatoms, wherein at least one ring comprises a heteroatom, and wherein the other ring may for example be a carbocyclic ring, e.g. isoindolyl.

The term "cycloalkenyl" is intended to indicate mono-, di- tri- or tetraunsaturated non-aromatic cyclic hydrocarbon radicals, comprising 3-20 carbon atoms, including fused bicyclic rings, typically comprising 3-10 carbon atoms, such as 3, 4, or 6 carbon atoms, e.g. cyclopropenyl, cyclobutenyl, cyclopentenyl, cyclohexenyl, cylcoheptenyl.

The term "heterocycloalkenyl" is intended to indicate a cycloalkene radical as described above, wherein one or more carbon atoms are replaced by heteroatoms, comprising 1-19 carbon atoms, e.g. 2-4 carbon atoms, further comprising 1-6 heteroatoms, preferably 1, 2, or 3 heteroatoms, selected from O, N, or S, including fused bicyclic rings with 1-4 heteroatoms, wherein at least one ring comprises a heteroatom and wherein the other ring may for example be a carbocyclic ring, e.g. dihydrofuranyl, or 2,5-dihydro-1H-pyrrolyl.

The term "arylalkyl" is intended to indicate an aryl radical as defined above covalently joined to an alkyl group, e.g. benzyl.

The term "heteroarylalkyl" is intended to indicate a heteroaryl radical as defined above covalently joined to an alkyl group.

The term "halogen" is intended to indicate a substituent from the 7$^{th}$ main group of the periodic table, such as fluoro, chloro, bromo and iodo.

The term "haloalkyl" is intended to indicate an alkyl group as defined above substituted with one or more halogen atoms as defined above, e.g. difluoromethyl.

The term "hydroxyalkyl" is intended to indicate an alkyl group as defined above substituted with one or more hydroxy, e.g. hydroxymethyl, hydroxyethyl, hydroxypropyl.

The term "alkoxy" is intended to indicate a radical of the formula —OR', wherein R' is alkyl as indicated above, e.g. methoxy, ethoxy, n-propoxy, isopropoxy, butoxy, etc.

The term "alkoxycarbonyl" is intended to indicate a radical of the formula —C(O)—O—R', wherein R' is alkyl as indicated above, e.g. methoxycarbonyl, ethoxycarbonyl, n-propoxycarbonyl, isopropoxycarbonyl, etc.

The term "alkylcarbonyl" is intended to indicate a radical of the formula —C(O)—R', wherein R' is alkyl as indicated above, e.g. ethanoyl, acetyl.

The term "heterocyclic ring" is intended to indicate a heteroaryl, heterocycloalkyl and heterocycloalkenyl, wherein one or more carbon atoms are replaced by heteroatoms, comprising 1-19 carbon atoms, e.g. 2-4 carbon atoms, further comprising 1-6 heteroatoms, preferably 1,2, or 3 heteroatoms, selected from O, N, or S, which may optionally be oxidised once or twice, e.g. [1,3]dioxole, oxetane, [1,3]dioxolane, [1,3]dioxane, tetrahydrothiopyran, tetrahydrothiopyran-1,1-dioxide, tetrahydrothiopyran-1-oxide, piperidine, tetrahydrothiophene, [1,3]-dithiane, thietane, [1,3]-dithiane-1,3-dioxide, or thietane-1-oxide, or including fused bicyclic rings with 1-4 heteroatoms, wherein at least one ring comprises a heteroatom, and wherein the other ring may for example be a carbocyclic ring, e.g. isoindolyl.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, silver hydroxide, ammonia or the like, or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylene-diamine, and dibenzylamine, or L-arginine or L-lysine. Salts obtained by reaction with a suitable base include, but are not limited to sodium salts, choline salts, 2-(dimethylamino)-ethanol salts, 4-(2-hydroxyethyl)-morpholine salts, L-lysine salts, N-(2-hydroxyethyl)-pyrrolidine salts, ethanolamine salts, potassium salts, tetrabutylammonium salts, benzyltrimethylammonium salts, cetyltrimethylammonium salts, tetramethylammonium salts, tetrapropylammonium salts, tris (hydroxymethyl)aminomethane salts, N-methyl-D-glucamine salts, silver salts, benzethonium salts, and triethanolamine salts.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

Embodiments of the Invention

In currently favoured embodiments, the invention relates to compounds of general formula I wherein X is —CH$_2$— or —NH—.

In another embodiment, the invention relates to compounds of general formula IIa

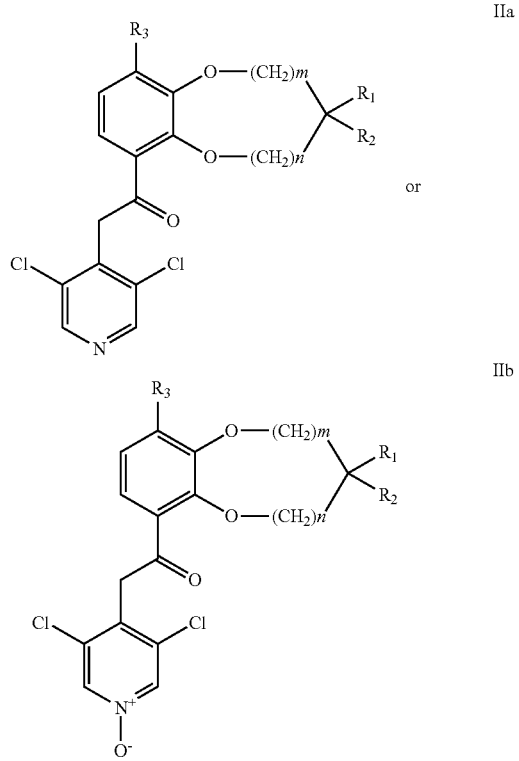

wherein m, n, R$_1$, R$_2$ and R$_3$ are as described above.

In one embodiment, m and n in formula IIa and IIb are both 0. In another embodiment, m and n in formula IIa and IIb are both 1.

In an embodiment, R$_3$ is —OCHF$_2$ or —OCF$_3$, such as —OCHF$_2$.

In another embodiment, R$_3$ is —SCHF$_2$ or —SCF$_3$.

In an embodiment, R$_1$ and R$_2$, together with the carbon atom to which they are attached, form a 4-, 5- or 6-membered heterocyclic ring. The heterocyclic ring may comprise one heteroatom, e.g. selected from oxygen or —S(O)$_2$. Specific examples of heterocyclic rings are tetrahydropyran, oxetane, [1,3]dioxolane, [1,3]dioxane, tetrahydrothiopyran, tetrahydrothiopyran-1,1-dioxide, tetrahydrothiopyran-1-oxide, tetrahydrothiophene, [1,3]-dithiane, thietane, [1,3]-dithiane-1,3-dioxide, thietane-1-oxide, or thiethane-1,1-dioxide.

Specific examples of compounds of the invention are
2-(3,5-Dichloropyridin-4-yl)-1-{9-difluoromethoxy-spiro [2H-1,5-benzodioxepin-3(4H),3'-oxetane]-6-yl}ethanone (compound 101)
2-(3,5-Dichloro-1-oxido-pyridin-4-yl)-1-{9-difluoromethoxy-spiro[2H-1,5-benzodioxepin-3(4H),3'-oxetane]-6-yl}ethanone (compound 102)
2-(3,5-Dichloropyridin-4-yl)-1-{9-difluoromethoxy-spiro [2H-1,5-benzodioxepin-3(4H),4'-tetrahydropyran]-6-yl}ethanone (compound 103)
2-(3,5-Dichloro-1-oxido-pyridin-4-yl)-1-{9-difluoromethoxy-spiro[2H-1,5-benzodioxepin-3(4H),4'-tetrahydropyran]-6-yl}ethanone (compound 104)
2-(3,5-Dichloropyridine-4-yl)-1-(7-difluoromethoxy-2',3', 5',6'-tetrahydro-spiro[1,3-benzodioxole-2,4'-(4H)-pyran]-4-yl)ethanone (compound 105)

2-(3,5-Dichloro-1-oxido-pyridine-4-yl)-1-(7-difluoromethoxy-2',3',5',6'-tetrahydro-spiro[1,3-benzodioxole-2,4'-(4H)-pyran]-4-yl)ethanone (compound 106)

2-(3,5-Dichloropyridine-4-yl)-1-(7-difluoromethoxy-2',3',5',6'-tetrahydro-spiro[1,3-benzodioxole-2, 4'-(4H)-thiopyran]-4-yl)ethanone (compound 107)

2-(3,5-Dichloro-1-oxido-pyridine-4-yl)-1-(7-difluoromethoxy-2',3',5',6'-tetrahydro-spiro[1,3-benzodioxole-2, 4'-(4H)-thiopyran-1',1'-dioxide]-4-yl)ethanone (compound 108)

2-(3,5-Dichloropyridine-4-yl)-1-(7-difluoromethoxy-2',3',5',6'-tetrahydro-spiro[1,3-benzodioxole-2, 4'-(4H)-thiopyran-1',1'-dioxide]-4-yl)ethanone (compound 109)

N-(3,5-Dichloro-4-pyridyl)-7-Difluoromethoxy-2',3',5',6'-tetrahydro-spiro[1,3-benzodioxole-2,4'-(4H)-thiopyran]-4-carbamide (compound 110)

N-(3,5-dichloro-1-oxo-4-pyridyl)-7-(difluoromethoxy)-1',1'-dioxo-spiro[1,3-benzodioxole-2,4'-thiane]-4-carboxamide (compound 111)

The compounds of the present invention may typically have a molecular weight below 800 Dalton, such as below 750 Dalton, e.g. below 700 Dalton, or below 650, 600, 550, or 500 Dalton.

The compounds of the invention may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

Compounds of the invention may or may not comprise asymmetrically substituted (chiral) carbon atoms which give rise to the existence of isomeric forms, e.g. enantiomers and possibly diastereomers. The present invention relates to all such isomers, either in pure form or as mixtures thereof (e.g. racemates). Pure stereoisomeric forms of the compounds and the intermediates of this invention may be obtained by the application of procedures known in the art. The various isomeric forms may be separated by physical separation methods such as selective crystallization and chromatographic techniques, e.g. liquid chromatography using chiral stationary phases. Enantiomers may be separated from each other by the selective crystallization of their diastereomeric salts with optically active amines, such as I-ephedrine. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably, if a specific stereoisomer is desired, said compound will be synthesized by stereoselective or stereospecific methods of preparation. These methods will advantageously employ chiral pure starting materials.

Compounds of the invention, optionally in combination with other active compounds, may be useful for the treatment of dermal diseases or conditions, or acute or chronic cutaneous wound disorders, in particular for the treatment of proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

Besides being useful for human treatment, the compounds of the present invention may also be useful for veterinary treatment of animals including mammals such as horses, cattle, sheep, pigs, dogs, and cats.

For use in therapy, compounds of the present invention are typically in the form of a pharmaceutical composition. The invention therefore relates to a pharmaceutical composition comprising a compound of formula Ia or Ib, optionally together with one or more other therapeutically active compound(s), together with a pharmaceutically acceptable excipient or vehicle. The excipient must be "acceptable" in the sense of being compatible with the other ingredients of the composition and not deleterious to the recipient thereof.

Conveniently, the active ingredient comprises from 0.05-99.9% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.1 mg and 1000 mg, preferably between 1 mg and 100 mg, such as 5-50 mg of a compound of formula I.

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.01 to 400 mg/kg body weight. The compound may be administered as a bolus (i.e. the entire daily dosis is administered at once) or in divided doses two or more times a day.

In the context of topical treatment it may be more appropriate to refer to a "usage unit", which denotes a single dose which is capable of being administered to a patient, and which may be readily handled and packed, remaining as a physically and chemically stable unit dose comprising either the active material as such or a mixture of it with solid or liquid pharmaceutical diluents or carriers.

The term "usage unit" in connection with topical use means a unitary, i.e. a single dose capable of being administered topically to a patient in an application per square centimetre of the infected area of from 0.1 mg to 10 mg, and preferably from 0.2 mg to 1 mg, of the active ingredient in question.

It is also envisaged that in certain treatment regimes, administration with longer intervals, e.g. every other day, every week, or even with longer intervals may be beneficial.

If the treatment involves administration of another therapeutically active compound it is recommended to consult *Goodman & Gilman's The Pharmacological Basis of Therapeutics*, 9th Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral (including sustained or timed release), rectal, parenteral (including subcutaneous, intraperitoneal, intramuscular, intraarticular and intravenous), transdermal, ophthalmic, topical, dermal, nasal or buccal administration. Topical administration of the claimed formulation is particularly suitable.

The formulations may conveniently be presented in dosage unit form and may be pre-pared by any of the methods well known in the art of pharmacy, e.g. as disclosed in *Remington, The Science and Practice of Pharmacy*, 20$^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical or ophthalmic administration include liquid or semi-liquid preparations such as liniments, lotions, gels, sprays, foams, oil-in-water or water-in-oil emulsions such as creams, ointments or pastes; or solutions or suspensions such as drops. Compositions for ophthalmic treatment may preferably additionally contain a cyclodextrin.

For topical administration, the compound of formula I may typically be present in an amount of from 0.01 to 20% by weight of the composition, such as 0.1% to about 10%, but may also be present in an amount of up to about 50% of the composition.

Formulations suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T. Rhodes (Eds.), page 427-432, Marcel Dekker, New York; Modern Pharmaceutics, $3^{th}$ ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

The pharmaceutical composition may additionally comprise one or more other active components conventionally used in the treatment of dermal disease or conditions, e.g. selected from the group consisting of glucocorticoids, vitamin D and vitamin D analogues, antihistamines, platelet activating factor (PAF) antagonists, anticholinergic agents, methylxanthines, β-adrenergic agents, COX-2 inhibitors, salicylates, indomethacin, flufenamate, naproxen, timegadine, gold salts, penicillamine, serum cholesterol lowering agents, retinoids, zinc salts, salicylazosulfapyridine and calcineurin inhibitors.

The invention is described in further detail in the following examples which are not in any way intended to limit the scope of the invention as claimed.

METHODS OF PREPARATION

The compounds of the present invention can be prepared in a number of ways well known to those skilled in the art of synthesis. The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used.

Starting materials are either known compounds which are commercially available, or they may be prepared by routine synthetic methods well known to a person skilled in the art.

The compounds of the present invention or any intermediate may be purified if required using standard methods well known to a synthetic organist chemist, e.g. methods described in "Purification of Laboratory Chemicals", 5th ed. 2003. Starting materials are either known compounds, commercially available, or they may be prepared by routine synthetic methods well known to a person skilled in the art.

GENERAL PROCEDURES, PREPARATIONS AND EXAMPLES $^1$H nuclear magnetic resonance (NMR) spectra were recorded at 300 MHz and $^{13}$C NMR spectra at 75.6 MHz. Chemical shift values (δ, in ppm) are quoted in the specified solvent relative to internal tetramethylsilane (δ=0.00) or chloroform (δ=7.25) or deuteriochloroform (δ=76.81 for $^{13}$C NMR) standards. The value of a multiplet, either defined (doublet (d), triplet (t), quartet (q)) or not (m) at the approximate mid point is given unless a range is quoted. (bs) indicates a broad singlet. The organic solvents used were usually anhydrous. Chromatography was performed on Merck silica gel 60 (0.040-0-063 mm). The solvent ratios indicated refer to v:v unless otherwise noted.

The following abbreviations have been used throughout:
DCM dichloromethane
DMF N,N'-Dimethylformamide
DMSO dimethyl sulfoxide
Et ethyl
EtOAc ethyl acetate
h hour
L liter
LDA lithium diisopropylamide
LiHMDS lithium Hexamethyldisilazide
m milli
Me methyl
MeOH methanol
NMR nuclear magnetic resonance
ppt precipitate
rt room temperature
TsCl p-toluenesulphonyl chloride
THF tetrahydrofuran
v volume
Preparative HPLC/MS Preparative HPLC/MS was performed on a Dionex APS-system with two Shimadzu PP150 prep. pumps and a Thermo MSQ Plus mass spectrometer. Column: Waters XTerra C-18, 150 mm×19 mm, 5 μm; solventsystem: A=water (0.1% formic acid) and B=acetonitrile (0.1% formic acid); flow rate=18 mL/min; method (10 min): Linear gradient method going from 10% B to 100% B in 6 minutes and staying at 100% B for another 2 minutes. The fractions were collected based on ion traces of relevant ions and PDA signal (240-400 nm).
Analytical HPLC/MS Method A: Analytical HPLC/MS was performed on a Dionex APS-system with a P680A analytical pump and a Thermo MSQ Plus mass spectrometer. Column: Waters XTerra C-18, 150 mm×4.6 mm, 5 μm; solventsystem: A=water (0.1% formic acid) and B=acetonitrile (0.1% formic acid); flow rate=1.0 mL/min; method (10 min): Linear gradient method going from 10% B to 100% B in 6.6 minutes and staying at 100% B for another 1.5 minutes.

Method B: Analytical HPLC/MS was performed on a system consisting of a Waters 2795 HPLC, Micromass ZQ mass spectrometer, Waters 996 PDA. Column: Waters XTerra C-18, 50 mm×3.0 mm, 5 μm; solventsystem: A=water:acetonitrile 95:5 (0.05% formic acid) and B=acetonitrile (0.05% formic acid); flow rate=1.0 mL/min; method (8 min): Linear gradient method going from 10% B to 100% B in 6.0 minutes and staying at 100% B for 1 minute.
General Procedure of Preparation:

The compounds of the invention can for example be prepared as follows. Compounds of the general formula IIa and IIb, wherein n, m, $R_1$, $R_2$ are as defined above and $R_3$=OCF$_2$H can be prepared as follows:

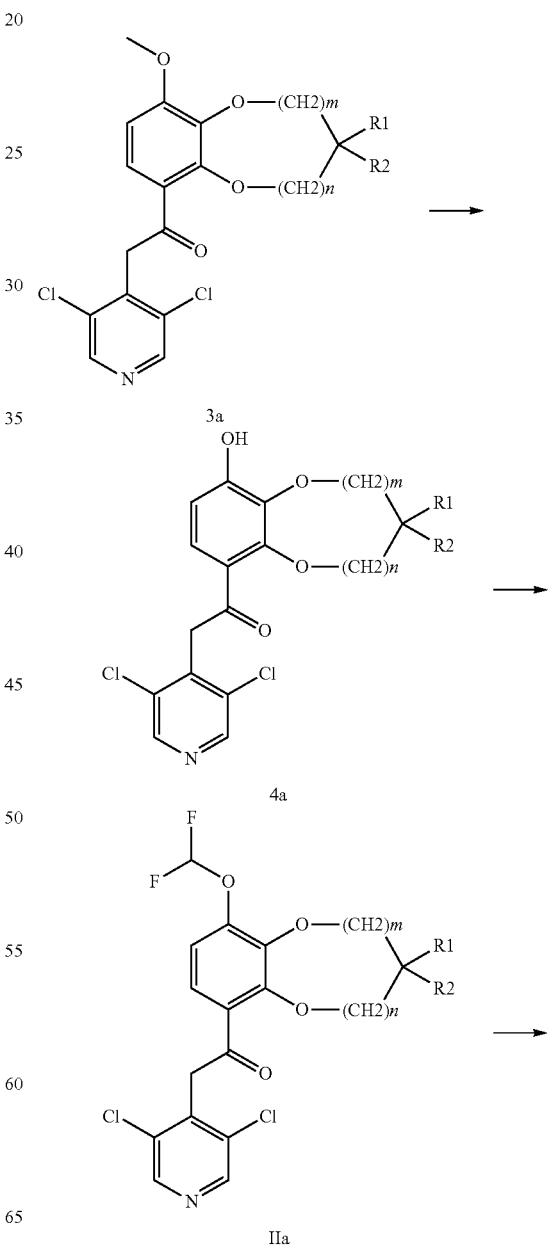

-continued

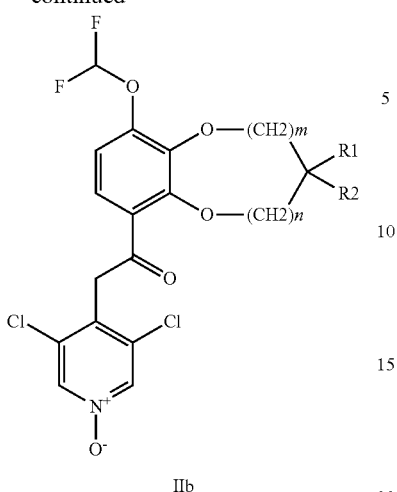

IIb

Starting materials of formula 3a are prepared according to standard procedures known to a person skilled in the art (WO 2008/104175). Selective de-alkylation of 3a using a sulphur nucleophile e.g. t-dodecyl mercaptane affords 4a.

Reaction of compounds with formula 4a with sodium chlorodifluoroacetate in the presence of a base e.g. $K_2CO_3$ in a suitable solvent such as DMF at temperatures from room temperature to 140° C. give compounds of the formula IIa.

Oxidation of IIa with 3-chloroperbenzoic acid or $H_2O_2$/methyltrioxorhenium(VII) in a suitable solvent such as DCM afforded compounds of the general formula IIb Compounds of the general formula I wherein X=—NH— can for example be prepared as described in WO 2008/104175, which is hereby incorporated by reference, and as described in example 10 and example 11 in the present application.

Preparation 1

2-(3,5-Dichloropyridin-4-yl)-1-{9-hydroxy-spiro [2H-1,5-benzodioxepin-3(4H), 3'-oxetane]-6-yl}ethanone (compound 401)

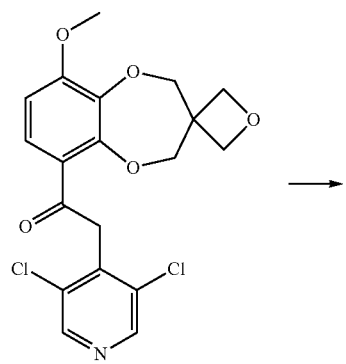

-continued

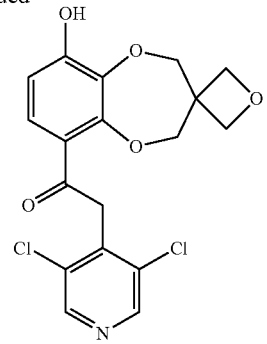

A solution of 2-(3,5-Dichloropyridin-4-yl)-1-{9-methoxyspiro[2H-1,5-benzodioxepin-3(4H),3'-oxetane]-6-yl}ethanone (272 mg, 0.7 mmol) in anhydrous DMF (4 mL) was added K2CO3 (916 mg, 7 mmol) and t-dodecyl mercaptan (3.12 ml, 13 mmol). The mixture was heated, with stirring, at 140° C. in a sealed tube for 16 h. The mixture was allowed to cool to r.t. and water (20 ml) was added. After neutralisation with 4N HCl the mixture was extracted with DCM. The combined organic phase was washed with brine, dried over MgSO4 and evaporated to dryness under reduced pressure. Chromatography yielded the product 401.

$^1$H NMR (300 MHz, DMSO) δ 8.65 (s, 2H), 7.36 (d, J=8.8 Hz, 1H), 6.68 (d, J=8.8 Hz, 1H), 4.64 (s, 2H), 4.54 (s, 2H), 4.53-4.42 (m, 4H), 4.33 (s, 2H).

Example 1

2-(3,5-Dichloropyridin-4-yl)-1-{9-difluoromethoxyspiro[2H-1,5-benzodioxepin-3(4H),3'-oxetane]-6-yl}ethanone (compound 101)

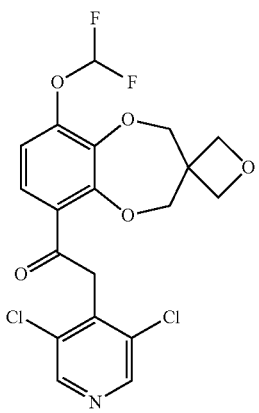 [SMILES: O=C(Cc1c(Cl)cncc1Cl)c1ccc(OC(F)F)c2c1OCC1(COC1)CO2]

A solution of 2-(3,5-Dichloropyridin-4-yl)-1-{9-hydroxy-spiro[2H-1,5-benzodioxepin-3(4H),3'-oxetane]-6-yl}ethanone [401](1.66 g, 4.2 mmol) in DMF (12 mL) and water (1.3 ml) was added K2CO3 (1.45 g, 10.5 mmol) and sodium chlorodifluoroacetate (1.28 g, 8.4 mmol). The mixture was heated under Argon, with stirring, at 100° C. in a sealed tube for 1.5 h. Additional 950 mg of sodium chlorodifluoroacetate was added and heating was continued for 1 h.

Additional 950 mg of sodium chlorodifluoroacetate and 1.45 g K2CO3 was added, heating continued for 5 h. Another portion of 950 mg of sodium chlorodifluoroacetate and 1.45 g K2CO3 was added, heating continued for 2 h. The mixture was allowed to cool to rt, added water (200 ml) and pH was adjusted to 3 using 4N HCl. The mixture was extracted with DCM and the combined organic phase was washed with brine, dried over MgSO4 and evaporated to dryness under reduced pressure. Chromatography yielded 793 mg of the product 101.

$^1$H NMR (300 MHz, CDCl3) δ 8.51 (s, 2H), 7.46 (d, J=8.7 Hz, 1H), 6.96 (d, J=8.7 Hz, 1H), 6.64 (t, J=74 Hz, 1H), 4.68-4.56 (m, 8H), 4.56-4.46 (bs, 2H).

Example 2

2-(3,5-Dichloro-1-oxido-pyridin-4-yl)-1-{9-difluoromethoxy-spiro[2H-1,5-benzodioxepin-3(4H),3'-oxetane]-6-yl}ethanone (compound 102)

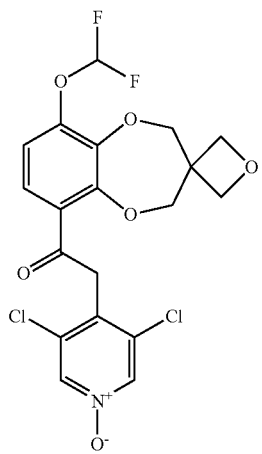 [SMILES: O=C(Cc1c(Cl)c[n+]([O-])cc1Cl)c1ccc(OC(F)F)c2c1OCC1(COC1)CO2]

A solution of 2-(3,5-Dichloropyridin-4-yl)-1-{9-difluoromethoxy-spiro[2H-1,5-benzodioxepin-3(4H),3'-oxetane]-6-yl}ethanone [101] (792 mg, 1.8 mmol) in DCM (15 ml) was added 3-chloroperbenzoic acid (1.2 g, 7 mmol) and the mixture was stirred at rt for 4 h. Additional 3-chloroperbenzoic acid (0.6 g, 3.5 mmol) was added and stirring was continued for 16 h. The reaction mixture was washed with Na2CO3 and subsequently brine, dried over MgSO4 and evaporated to dryness under reduced pressure. Chromatography yielded an almost pure product which subsequently was suspended in EtOAc and filtered off yielding 464 mg of 102

$^1$H NMR (300 MHz, CDCl3) δ 8.22 (s, 2H), 7.47 (d, J=8.8 Hz, 1H), 6.97 (d, J=8.8 Hz, 1H), 6.63 (t, J=74 Hz, 1H), 4.70-4.59 (m, 6H), 4.56 (bs, 2H), 4.52 (bs, 2H).

Preparation 2

2-(3,5-Dichloropyridin-4-yl)-1-{9-hydroxy-spiro[2H-1,5-benzodioxepin-3(4H),4'-tetrahydropyran]-6-yl}ethanone (compound 402)

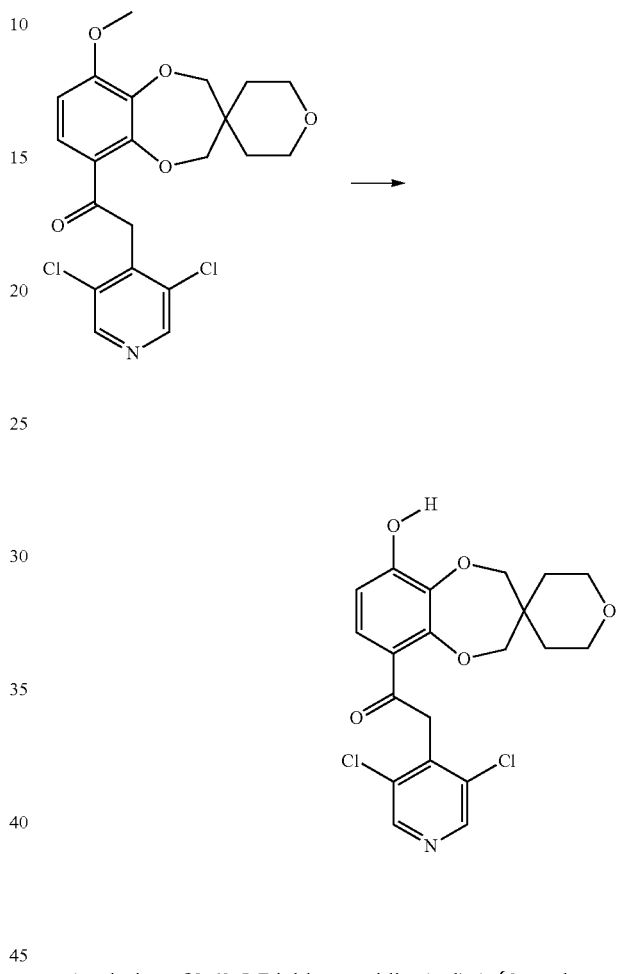

A solution of 2-(3,5-Dichloropyridin-4-yl)-1-{9-methoxy-spiro[2H-1,5-benzodioxepin-3(4H),4'-tetrahydropyran]-6-yl}ethanone (351 mg, 0.8 mmol) in anhydrous DMF (6 mL) was added K2CO3 (1.1 g, 8 mmol) and t-dodecyl mercaptan (3.8 ml, 16 mmol). The mixture was heated, with stirring, at 140° C. in a sealed tube for 22 h. The mixture was allowed to cool to r.t. and water was added. After neutralisation with 4N HCl the mixture was extracted with DCM (2×50 ml). The combined organic phase was extracted twice with 2N NaOH. The aqueous phase was washed twice with DCM, neutralised with 4N HCL and finally extracted with DCM. The organic phase was washed with brine, dried over MgSO4 and evaporated to dryness under reduced pressure. Chromatography yielded the product 402 as a yellow powder (118 mg)

$^1$H NMR (300 MHz, CDCl3) δ 8.49 (s, 2H), 7.51 (d, J=8.8 Hz, 1H), 6.70 (d, J=8.8 Hz, 1H), 6.30 (s, 1H), 4.60 (s, 2H), 4.27 (s, 2H), 4.21 (s, 2H), 3.91-3.55 (m, 4H), 1.76 (t, J=5.5 Hz, 4H).

Example 3

2-(3,5-Dichloropyridin-4-yl)-1-{9-difluoromethoxy-spiro[2H-1,5-benzodioxepin-3(4H),4'-tetrahydropyran]-6-yl}ethanone (compound 103)

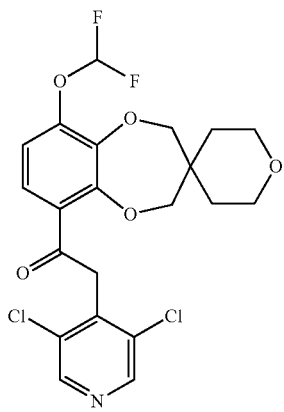 [SMILES: O=C(Cc1c(Cl)cncc1Cl)c1ccc(OC(F)F)c2c1OCC1(CCOCC1)CO2]

A solution of 2-(3,5-Dichloropyridin-4-yl)-1-{9-hydroxy-spiro[2H-1,5-benzodioxepin-3(4H),4'-tetrahydropyran]-6-yl}ethanone [402] (118 mg, 0.28 mmol) in anhydrous DMF (6 mL) was added K2CO3 (76 mg, 0.55 mmol) and sodium chlorodifluoroacetate (84 mg, 0.55 mmol). The mixture was heated under Argon, with stirring, at 100° C. in a sealed tube for 1.5 h. Additional K2CO3 (76 mg, 0.55 mmol) and sodium chlorodifluoroacetate (84 mg, 0.55 mmol) was added and stirring was continued at 80° C. for 6 h. The mixture was allowed to cool to rt, added water and the mixture was neutralised using 4N HCl. The mixture was extracted with DCM and the combined organic phase was washed with brine, dried over MgSO4 and evaporated to dryness under reduced pressure. Chromatography yielded 40 mg of the product 103.

$^1$H NMR (300 MHz, CDCl3) δ 8.50 (s, 2H), 7.44 (d, J=8.7 Hz, 1H), 6.91 (d, J=8.7 Hz, 1H), 6.63 (t, J=74 Hz, 1H), 4.62 (s, 2H), 4.27 (s, 2H), 4.22 (s, 2H), 3.87-3.58 (m, 4H), 1.85-1.62 (m, 4H).

Example 4

2-(3,5-Dichloro-1-oxido-pyridin-4-yl)-1-{9-difluoromethoxy-spiro[2H-1,5-benzodioxepin-3(4H),4'-tetrahydropyran]-6-yl}ethanone (compound 104)

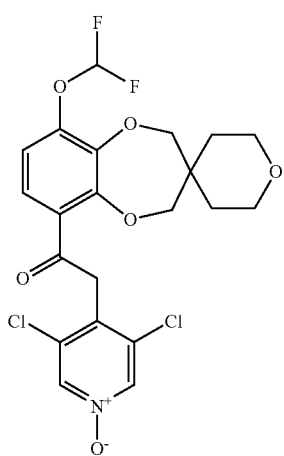 [SMILES: O=C(Cc1c(Cl)c[n+]([O-])cc1Cl)c1ccc(OC(F)F)c2c1OCC1(CCOCC1)CO2]

A solution of 2-(3,5-Dichloropyridin-4-yl)-1-{9-difluoromethoxy-spiro[2H-1,5-benzodioxepin-3(4H),4'-tetrahydropyran]-6-yl}ethanone [103] (37 mg, 0.08 mmol) in DCM (3 ml) was added 3-chloroperbenzoic acid (54 mg, 0.3 mmol) and the mixture was stirred at rt for 16 h. Additional 3-chloroperbenzoic acid (27 mg, 0.18 mmol) was added and stirring was continued for 5 h. The reaction mixture was washed with Na2CO3 and subsequently brine, dried over MgSO4 and evaporated to dryness under reduced pressure. Chromatography yielded 33 mg of the product 104.

$^1$H NMR (600 MHz, CDCl3) δ 8.21 (s, 2H), 7.45 (d, J=8.8 Hz, 1H), 6.93 (d, J=8.7 Hz, 1H), 6.64 (t, J=74 Hz, 1H), 4.55 (s, 2H), 4.28 (s, 2H), 4.24 (s, 2H), 3.86-3.61 (m, 4H), 1.89-1.64 (m, 4H).

Preparation 3

2-(3,5-Dichloropyridine-4-yl)-1-(7-hydroxy-2',3',5',6'-tetrahydro-spiro[1,3-benzodioxole-2,4'-(4H)-pyran]-4-yl)ethanone (compound 403)

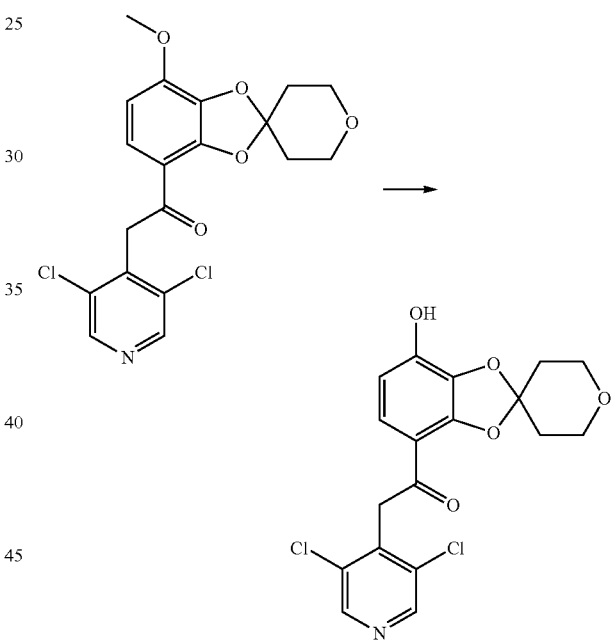

A solution of 2-(3,5-Dichloropyridine-4-yl)-1-(7-methoxy-2',3',5',6'-tetrahydro-spiro[1,3-benzodioxole-2,4'-(4H)-pyran]-4-yl)ethanone (325 mg, 0.8 mmol) in anhydrous DMF (5 ml) was added K2CO3 (1.1 g, 8 mmol) and t-dodecyl mercaptan (3.7 ml, 16 mmol). The mixture was heated, with stirring, at 140° C. in a sealed tube for 16 h. The mixture was allowed to cool to r.t. and water was added. After neutralisation with 4N HCl the mixture was extracted with DCM (2×50 ml). The combined organic phase was extracted twice with 2N NaOH. The aqueous phase was washed twice with DCM, neutralised with 4N HCL and finally extracted with DCM (3×75 ml). The organic phase was dried over MgSO4 and evaporated to dryness under reduced pressure. Chromatography yielded the product 403 as a white powder (192 mg)

$^1$H NMR (300 MHz, DMSO) δ 8.65 (s, 2H), 7.95 (s, 1H), 7.25 (d, J=9.0 Hz, 1H), 6.56 (d, J=8.9 Hz, 1H), 4.59 (s, 2H), 3.92-3.67 (m, 4H), 2.21-1.94 (m, 4H).

Example 5

2-(3,5-Dichloropyridine-4-yl)-1-(7-difluoromethoxy-2',3',5',6'-tetrahydro-spiro[1,3-benzodioxole-2,4'-(4H)-pyran]-4-yl)ethanone (compound 105)

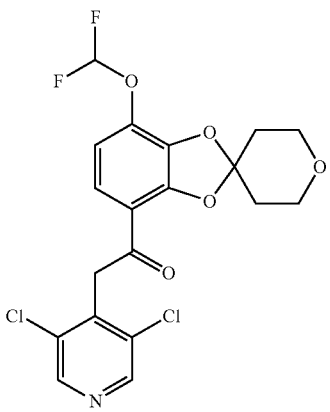 [SMILES: O=C(Cc1c(Cl)cncc1Cl)c1ccc(OC(F)F)c2c1OC1(CCOCC1)O2]

A solution of 2-(3,5-Dichloropyridine-4-yl)-1-(7-hydroxy-2',3',5',6'-tetrahydro-spiro[1,3-benzodioxole-2,4'-(4H)-pyran]-4-yl)ethanone [403] (188 mg, 0.47 mmol) in anhydrous DMF (10 mL) was added K2CO3 (98 mg, 0.7 mmol) and sodium chlorodifluoroacetate (108.5 mg, 0.7 mmol). The mixture was heated under Argon, with stirring, at 100° C. in a sealed tube for 45 min. Additional K2CO3 (65 mg, 0.47 mmol) and sodium chlorodifluoroacetate (72 mg, 0.47 mmol) was added and stirring was continued at 100° C. for 30 min. The mixture was allowed to cool to rt, filtered and evaporated to dryness under reduced pressure. HPLC purification yielded Chromatography yielded 89 mg of the product 105.

$^1$H NMR (300 MHz, CDCl3) δ 8.52 (s, 2H), 7.46 (d, J=9.1 Hz, 1H), 6.81 (d, J=9.0, 1H), 6.74 (t, J=73 Hz, 1H), 4.60 (s, 2H), 4.05-3.83 (m, 4H), 2.21 (t, J=5.5 Hz, 4H).

Example 6

2-(3,5-Dichloro-1-oxido-pyridine-4-yl)-1-(7-difluoromethoxy-2',3',5',6'-tetrahydro-spiro[1,3-benzodioxole-2,4'-(4H)-pyran]-4-yl)ethanone (compound 106)

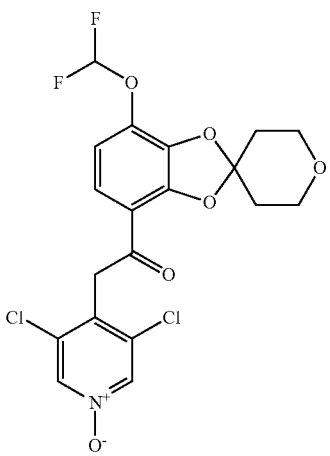 [SMILES: O=C(Cc1c(Cl)c[n+]([O-])cc1Cl)c1ccc(OC(F)F)c2c1OC1(CCOCC1)O2]

To a solution of 2-(3,5-Dichloropyridine-4-yl)-1-(7-difluoromethoxy-2',3',5',6'-tetrahydro-spiro[1,3-benzodioxole-2,4'-(4H)-pyran]-4-yl)ethanone [105] (89 mg, 0.2 mmol) in dichloromethane (4 mL) was added 30% H2O2 (68 μL, 0.6 mmol) and methyltrioxorhenium(VII) (25 mg). The mixture was stirred at room temperature overnight, added MnO2 (5 mg) and was stirred for 10 min. After filtration and evaporated to dryness under reduced pressure, standard HPLC purification afforded 33 mg of the product 106.

$^1$H NMR (300 MHz, CDCl3) δ 8.22 (s, 2H), 7.46 (d, J=9.1 Hz, 1H), 6.81 (d, J=9.1 Hz, 1H), 6.74 (t, J=73 Hz, 1H), 4.53 (s, 2H), 4.08-3.88 (m, 4H) 2.21 (t, J=5.5 Hz, 4H).

Preparation 4

2-(3,5-Dichloropyridine-4-yl)-1-(7-hydroxy-2',3',5',6'-tetrahydro-spiro[1,3-benzodioxole-2, 4'-(4H)-thiopyran]-4-yl)ethanone (compound 404)

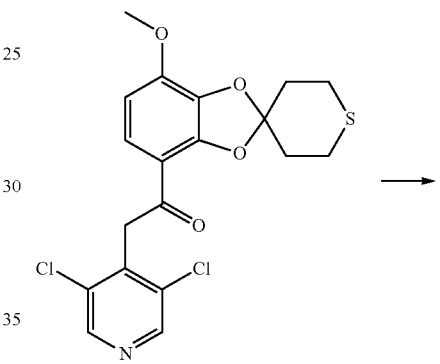

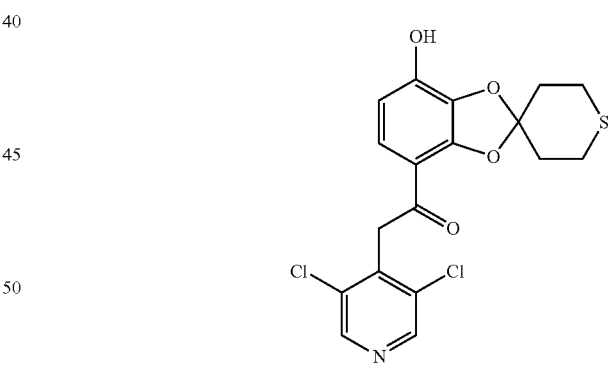

A solution of 2-(3,5-Dichloropyridine-4-yl)-1-(7-methoxy-2',3',5',6'-tetrahydro-spiro[1,3-benzodioxole-2, 4'-(4H)-thiopyran]-4-yl)ethanone (8.3 g, 19.5 mmol) in anhydrous DMF (80 mL) was added K2CO3 (27 g, 195 mmol) and t-dodecyl mercaptan (92 ml, 390 mmol). The mixture was heated, with stirring, at 140° C. in a sealed tube for 21 h. Additional K2CO3 (13 g) and t-dodecyl mercaptan (45 ml) was added. Stirring was continued for additional 5 h. The mixture was allowed to cool to r.t. and water was added. After neutralisation with 4N HCl the mixture was extracted with DCM (3×200 ml). The combined organic phase was washed with brine, dried over MgSO4 and evaporated to dryness under reduced pressure. Flash chromatography gave a crude product that was re-dissolved in DCM and subsequently extracted twice with 2N NaOH. The aqueous phase was washed twice with DCM, neutralised with 4N HCL and finally extracted with DCM (3×150 ml). The organic phase was washed with brine, dried over MgSO4 and evaporated to dryness under reduced pressure. Chromatography yielded 2.56 g of the product 404.

¹H NMR (300 MHz, CDCl3) δ 8.52 (s, 2H), 7.38 (d, J=9.0 Hz, 1H), 6.54 (d, J=9.0 Hz, 1H), 4.60 (s, 2H), 2.94-2.77 (m, 4H), 2.46-2.15 (m, 4H).

Example 7

2-(3,5-Dichloropyridine-4-yl)-1-(7-difluoromethoxy-2',3',5',6'-tetrahydro-spiro[1,3-benzodioxole-2, 4'-(4H)-thiopyran]-4-yl)ethanone (compound 107)

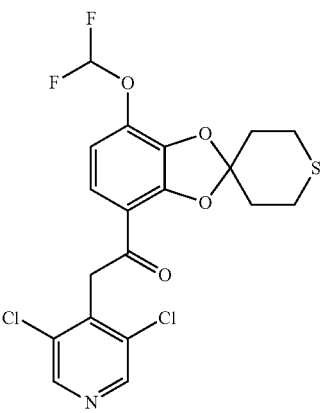 [SMILES: O=C(Cc1c(Cl)cncc1Cl)c1ccc(OC(F)F)c2c1OC1(CCSCC1)O2]

A solution of 2-(3,5-Dichloropyridine-4-yl)-1-(7-hydroxy-2',3',5',6'-tetrahydro-spiro[1,3-benzodioxole-2, 4'-(4H)-thiopyran]-4-yl)ethanone [404] (4.27 g, 10.4 mmol) in anhydrous DMF (120 mL) was added K2CO3 (2.16 g, 15.6 mmol) and sodium chlorodifluoroacetate (2.47 g, 15.6 mmol). The mixture was heated under Argon, with stirring, at 100° C. for 40 min. The mixture was allowed to cool to rt, added water (500 ml) and extracted with EtOAc (2×400 ml). The combined organic phase was washed with water (500 ml) and saturated NaCl solution (150 ml) followed by drying over Na2SO4 and evaporated to dryness under reduced pressure. Chromatography yielded 2.64 g of the product 107 a yellow-white powder.

¹H NMR (400 MHz, DMSO) δ 8.67 (s, 2H), 7.61-7.09 (m, 2H), 6.93 (d, J=9.0 Hz, 1H), 4.67 (s, 2H), 3.05-2.74 (m, 4H), 2.42-2.16 (m, 4H).

Example 8

2-(3,5-Dichloro-1-oxido-pyridine-4-yl)-1-(7-difluoromethoxy-2',3',5',6'-tetrahydro-spiro[1,3-benzodioxole-2, 4'-(4H)-thiopyran-1',1'-dioxide]-4-yl)ethanone (compound 108).

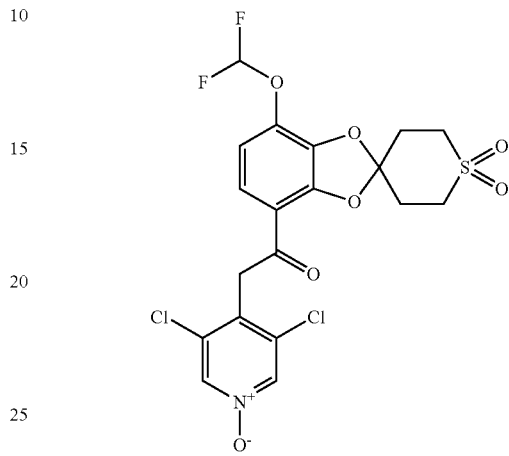

A solution of 2-(3,5-Dichloropyridine-4-yl)-1-(7-difluoromethoxy-2',3',5',6'-tetrahydro-spiro[1,3-benzodioxole-2, 4''-(4H)-thiopyran]-4-yl)ethanone [107] (2.64 g, 5.7 mmol) in chloroform (40 ml) was slowly added a solution of 3-chloroperbenzoic acid (5.76 g, 25.7 mmol) in chloroform (50 ml)—keeping the temperature between 21° C. and 24° C. The mixture was stirred at rt for 19 h and added to a NaHCO3(aq) solution. The organic phase was washed with an aqueous solution of NaCl. The aqueous phases were extracted with DCM. The combined organic phases was dried over Na2SO4 and evaporated to dryness under reduced pressure. Chromatography yielded 1.95 g of the product 108 as a white powder.

¹H NMR (300 MHz, CDCl3) δ 8.23 (s, 2H), 7.52 (d, J=9.1 Hz, 1H), 6.89 (d, J=9.1 Hz, 1H), 6.70 (t, J=72 Hz, 1H), 4.48 (s, 2H), 3.50-3.18 (m, 4H), 2.83-2.55 (m, 4H).

Preparation 5

2-(3,5-Dichloropyridine-4-yl)-1-(7-hydroxy-2',3',5', 6'-tetrahydro-spiro[1,3-benzo-dioxole-2, 4'-(4H)-thiopyran-1',1'-dioxide]-4-yl)ethanone (compound 405)

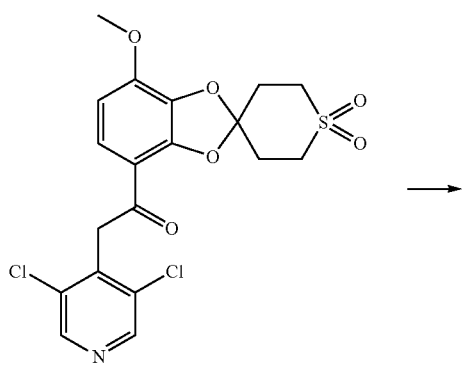

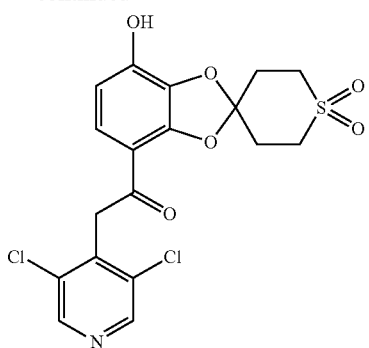

A solution of 2-(3,5-Dichloropyridine-4-yl)-1-(7-methoxy-2',3',5',6'-tetrahydro-spiro[1,3-benzodioxole-2, 4'-(4H)-thiopyran-1',1'-dioxide]-4-yl)ethanone (415 mg, 0.91 mmol) in anhydrous DMF (10 mL) was added K2CO3 (1.25 g, 9.1 mmol) and t-dodecyl mercaptan (4.3 ml, 18 mmol). The mixture was heated, with stirring, at 140° C. in a sealed tube for 16 h. The mixture was allowed to cool to r.t. and water was added. After neutralisation with 4N HCl the mixture was extracted with EtOAc (2×50 ml). The combined organic phase was extracted twice with 2N NaOH. The aqueous phase was washed twice with EtOAc, neutralised with 4N HCL and finally extracted with EtOAc (2×100 ml). The organic phase was washed with brine, dried over MgSO4 and evaporated to dryness under reduced pressure. Chromatography yielded 204 mg of the product 405.

¹H NMR (300 MHz, DMSO) δ 8.65 (s, 2H), 7.95 (s, 1H), 7.28 (d, J=9.0 Hz, 1H), 6.59 (d, J=8.9 Hz, 1H), 4.64 (s, 2H), 3.6-3.3 (m, 4H), 2.65-2.50 (m, 4H).

Example 9

2-(3,5-Dichloropyridine-4-yl)-1-(7-difluoromethoxy-2',3',5',6'-tetrahydro-spiro[1,3-benzodioxole-2, 4'-(4H)-thiopyran-1',1'-dioxide]-4-yl)ethanone (compound 109)

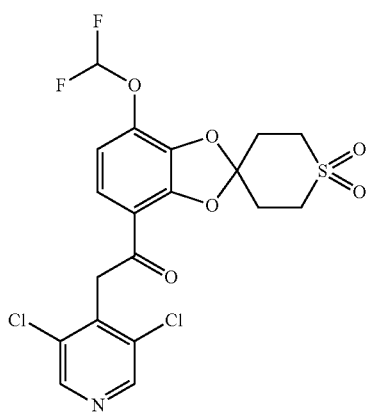 [SMILES: O=C(Cc1c(Cl)cncc1Cl)c1ccc(OC(F)F)c2c1OC1(CCS(=O)(=O)CC1)O2]

A solution of 2-(3,5-Dichloropyridine-4-yl)-1-(7-hydroxy-2',3",5",6"-tetrahydro-spiro[1,3-benzodioxole-2, 4'-(4H)-thiopyran-1',1'-dioxide]-4-yl)ethanone [405] (202 mg, 0.45 mmol) in anhydrous DMF (10 mL) was added K2CO3 (126 mg, 0.9 mmol) and sodium chlorodifluoroacetate (139 mg, 0.9 mmol). The mixture was heated under Argon, with stirring, at 100° C. for 1 h. Additional K2CO3 (63 mg, 0.45 mmol) and sodium chlorodifluoroacetate (69 mg, 0.45 mmol) was added and the reaction was heated for another hour. The mixture was allowed to cool to rt, filtered and evaporated to dryness under reduced pressure. Chromatography yielded 69 mg of the product 109.

¹H NMR (300 MHz, CDCl3) δ 8.53 (s, 2H), 7.52 (d, J=9.1 Hz, 1H), 6.89 (d, J~9 Hz, 1H), 6.69 (t, J=72 Hz, 1H), 4.56 (s, 2H), 3.56-3.15 (m, 4H), 2.91-2.50 (m, 4H).

Preparation 6

7-Difluoromethoxy-2',3',5',6'-tetrahydro-spiro[1,3-benzodioxole-2,4'-(4H)-thiopyran]-4-carboxylic acid

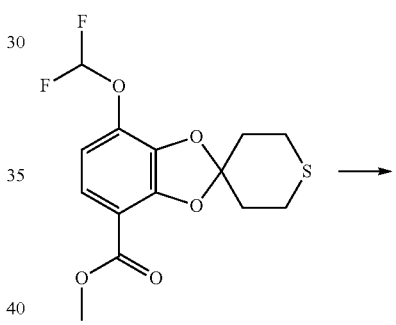

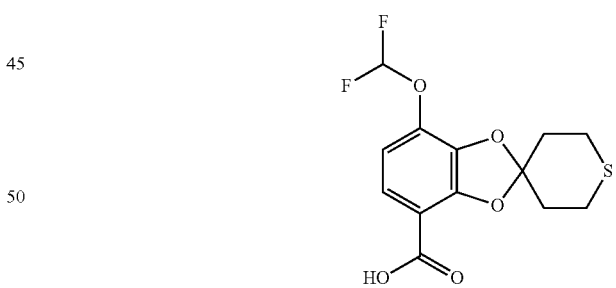

Methyl 7-Difluoromethoxy-2',3',5',6'-tetrahydro-spiro[1,3-benzodioxole-2,4'-(4H)-thiopyran]-4-carboxylate(437 mg) was dissolved in a mixture of Methanol(5 mL) and THF(5 mL) and 1M aqueous Lithium hydroxide(3.9 mL) was added. The ester was cleaved after 1 hour at 50° C. The solution was cooled to room temperature and acidified with 2N sulfuric acid (1.95 mL) and the product was extracted into EtOAc. 7-Difluoromethoxy-2',3',5',6'-tetrahydro-spiro[1,3-benzodioxole-2,4'-(4H)-thiopyran]-4-carboxylic acid was obtained after removal of solvents under reduced pressure.

Preparation 7

4-Nitrophenyl 7-difluoromethoxy-2',3',5',6'-tetrahydro-spiro[1,3-benzodioxole-2,4'-(4H)-thiopyran]-4-carboxylate

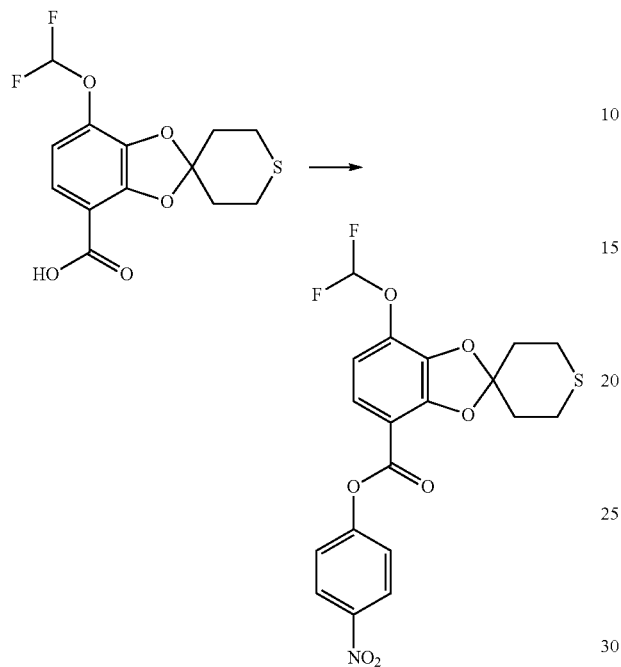

7-Difluoromethoxy-2',3',5',6'-tetrahydro-spiro[1,3-benzodioxole-2,4'-(4H)-thiopyran]-4-carboxylic acid (344 mg) was dissolved in dry DMF (3 mL). 4-Nitrophenol (226 mg) Ethyl-dimethylaminopropylcarbodiimide hydrochloride (312 mg) and N,N-Dimethyl-4-aminopyridine (198 mg) was added. After stirring at room temperature for 20 hours, aqueous work up with tert-Butyl methyl ether and chromatography of the organics in a gradient from 0 to 40% EtOAc in pentanes afforded the title compound as an oil.

Example 10

N-(3,5-Dichloro-4-pyridyl)-7-Difluoromethoxy-2',3',5',6'-tetrahydro-spiro[1,3-benzodioxole-2,4'-(4H)-thiopyran]-4-carbamide

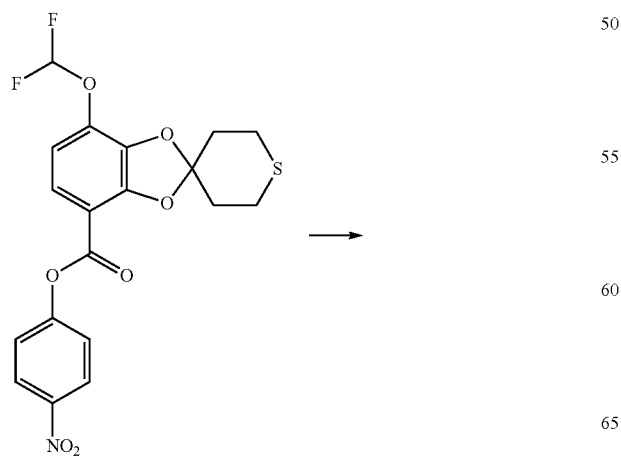

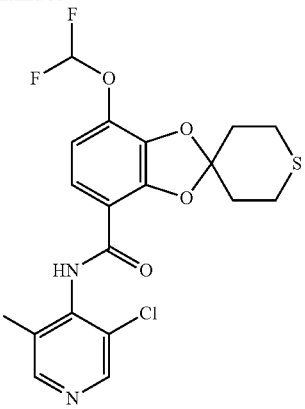

4-Nitrophenyl 7-difluoromethoxy-2',3',5',6'-tetrahydro-spiro[1,3-benzodioxole-2,4'-(4H)-thiopyran]-4-carboxylate (250 mg) and 3,5-Dichloro-4-aminopyridine (129 mg) was dissolved under argon in dry THF, 5 mL. Sodium hydride (50% suspension in oil), 40 mg, was added, and the mixture left stirring overnight. Aqueous work up with EtOAc and chromatography in a gradient from 0 to 60% EtOAc in pentane afforded the title compound. $^1$H NMR (300 MHz, CDCl3) δ 8.64 (s, 1H), 8.57 (s, 2H), 7.63 (d, J=9.0 Hz, 1H), 6.86 (d, J=9.1 Hz, 1H), 6.73 (t, J=72 Hz, 1H), 3.03-2.81 (m, 4H), 2.49-2.29 (m, 4H).

Example 11

N-(3,5-dichloro-1-oxo-4-pyridyl)-7-(difluoromethoxy)-1',1'-dioxo-spiro[1,3-benzodioxole-2,4'-thiane]-4-carboxamide

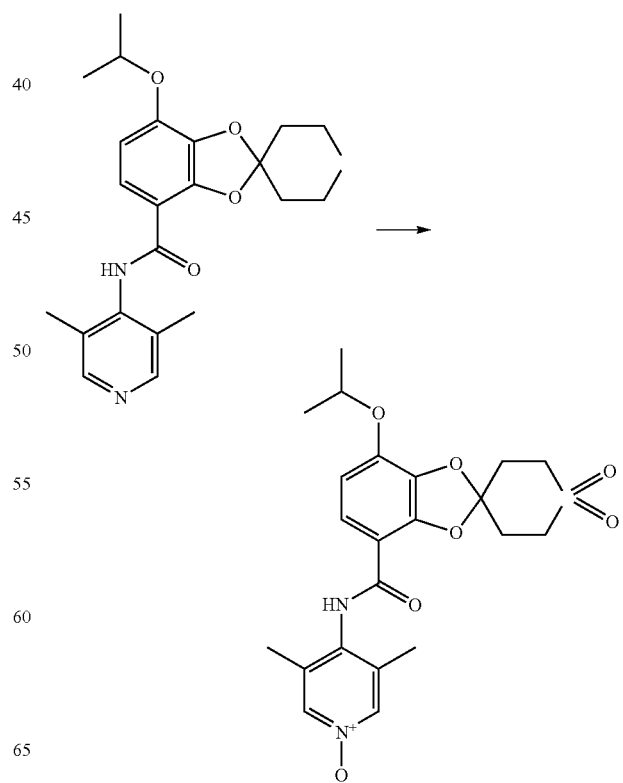

N-(3,5-Dichloro-4-pyridyl)-7-Difluoromethoxy-2',3',5',6'-tetrahydro-spiro[1,3-benzodioxole-2,4'-(4H)-thiopyran]-4-carbamide (157 mgq) was dissolved in formic acid, (1 mL) and cooled on ice. While stirring, Hydrogen peroxide (~50%)(0.260 mL) was added dropwise. The resulting solution was kept at room temperature overnight. The solution was poured into water and extracted three times with DCM. The extracts were concentrated under reduced pressure and purified by chromatography in a gradient of 0 to 10% Methanol in DCM, yielding the title compound. $^1$H NMR (300 MHz, DMSO) δ 9.46 (s, 1H), 8.76 (s, 2H), 7.46 (d, J=8.9 Hz, 1H), 7.39 (t, J=73.5 Hz, 1H), 6.98 (d, J=9.1 Hz, 1H), 3.76-3.56 (m, 2H), 3.34 (m, 2H), 2.75-2.53 (m, 4H).

Example 12

The following compounds wherein X=—NH— can for example be prepared as described in WO 2008/104175, and as described in example 10 and example 11 in the present application:

N-(3,5-dichloro-4-pyridyl)-6-(difluoromethoxy)spiro[2,4-dihydro-1,5-benzodioxepine-3,3'-oxetane]-9-carboxamide N-(3,5-dichloro-1-oxido-pyridin-1-ium-4-yl)-6-(difluoromethoxy)spiro[2,4-dihydro-1,5-benzodioxepine-3,3'-oxetane]-9-carboxamide N-(3,5-dichloro-4-pyridyl)-6-(difluoromethoxy)spiro[2,4-dihydro-1,5-benzodioxepine-3,4'-tetrahydropyran]-9-carboxamide N-(3,5-dichloro-1-oxido-pyridin-1-ium-4-yl)-6-(difluoromethoxy)spiro[2,4-dihydro-1,5-benzodioxepine-3,4'-tetrahydropyran]-9-carboxamide N-(3,5-dichloro-4-pyridyl)-7-(difluoromethoxy)spiro[1,3-benzodioxole-2,4'-tetrahydropyran]-4-carboxamide N-(3,5-dichloro-1-oxido-pyridin-1-ium-4-yl)-7-(difluoromethoxy)spiro[1,3-benzodioxole-2,4'-tetrahydropyran]-4-carboxamide N-(3,5-dichloro-4-pyridyl)-7-(difluoromethoxy)-1,1'-dioxo-spiro[1,3-benzodioxole-2,4'-thiane]-4-carboxamide N-(3,5-dichloro-1-oxido-pyridin-1-ium-4-yl)-6-(difluoromethoxy)-1',1'-dioxo-spiro[2,4-dihydro-1,5-benzodioxepine-3,3'-thietane]-9-carboxamide N-(3,5-dichloro-4-pyridyl)-6-(difluoromethoxy)-1',1'-dioxo-spiro[2,4-dihydro-1,5-benzodioxepine-3,3'-thietane]-9-carboxamide N-(3,5-dichloro-4-pyridyl)-6-(difluoromethoxy)spiro[2,4-dihydro-1,5-benzodioxepine-3,3'-thietane]-9-carboxamide N-(3,5-dichloro-1-oxido-pyridin-1-ium-4-yl)-6-(difluoromethoxy)spiro[2,4-dihydro-1,5-benzodioxepine-3,3'-thietane]-9-carboxamide N-(3,5-dichloro-4-pyridyl)-6-(difluoromethoxy)spiro[2,4-dihydro-1,5-benzodioxepine-3,3'-thietane]-9-carboxamide Example 13

The following compounds can be synthesized as described in the general procedure of preparation in the present application:

2-(3,5-dichloro-4-pyridyl)-1-[6-(difluoromethoxy)spiro[2,4-dihydro-1,5-benzodioxepine-3,3'-thietane]-9-yl]ethanone 2-(3,5-dichloro-1-oxido-pyridin-1-ium-4-yl)-1-[6-(difluoromethoxy)-1',1'-dioxo-spiro[2,4-dihydro-1,5-benzodioxepine-3,3'-thietane]-9-yl]ethanone 2-(3,5-dichloro-4-pyridyl)-1-[6-(difluoromethoxy)-1',1'-dioxo-spiro[2,4-dihydro-1,5-benzodioxepine-3,3'-thietane]-9-yl]ethanone 2-(3,5-dichloro-1-oxido-pyridin-1-ium-4-yl)-1-[6-(difluoromethoxy)spiro[2,4-dihydro-1,5-benzodioxepine-3,3'-thietane]-9-yl]ethanone Example 14

PDE4 Assay

Human recombinant PDE4 (Genbank accession no NM_006203) was incubated for 1 hour, with the test compound at concentrations up to 10 μM, with cAMP (1×10-5M), and with a low amount (0.021 MBq) of radioactively labelled cAMP. At the end of the incubation, the cleavage of the substrate was evaluated by the binding of the AMP product to SPA beads, which generate chemoluminescence when bound to the radioactive tracer. The AMP product inhibited the binding of the radioactive tracer to the beads, and the luminescent signal was competed.

The results were calculated as the molar concentrations resulting in 50% inhibition of the substrate cleavage compared to controls samples, and are expressed as $IC_{50}$ (M).

The results are shown in Table 1 below.

TABLE 1

| Compound | $IC_{50}$ (PDE4) |
|---|---|
| 101 | 6 nM |
| 102 | 13 nM |
| 103 | 6 nM |
| 104 | 4 nM |
| 105 | 7 nM |
| 106 | 5 nM |
| 108 | 16 nM |
| 109 | 13 nM |
| 110 | 2 nM |
| 111 | 106 nM |

Example 15

In Vivo Pharmacokinetic Analyses

One rat is dosed orally (5 mg/kg—dissolved in DMSO/H2O/propylenglycol [1:5:4]) and blood samples are taken from the sublingual venous plexus at 30 min, 1 h, 2 h, 4 h and 6 h. Blood samples are taken in BD Vacutainer SST serum separation tubes, serum is isolated by centrifugation, transferred to micronics tubes and subsequently analysed.

Mass spectrometer (API5000 series) parameters are optimised to analyse for the specific compounds and test injections are performed to confirm the validity of the established generic chromatography method. The generic method is based on fast gradient (2.5 min) analysis on C18 column with mobile phases consisting methanol, ammonium acetate, formic acid and water.

Standards are prepared in rat serum to cover the analytical range 0.1 to 300 ng/ml. Standards, blank serum and study samples are applied to 96 deepwell plate and proteins are precipitated by addition of acetonitrile containing internal standard. Samples are analysed on LC-MS/MS usually overnight. Integration and quantification is performed on ration between analyte and internal standard using Analyst software version 1.5. Pharmacokinetic parameters are calculated using a standardised Excel spreadsheet.

In vivo pharmacokinetic profile in rat of compound 101 disclosed in WO 2008/104175 and compound 105 and 106 disclosed in examples 5 and 6, respectively:

PO dosing of compound 101 from WO 2008/104175-5 mg/kg: Serum Cmax<3 ng/ml of parent compound, however serum Cmax~2000 ng/ml of the metabolite ($R_3$=OH). The PDE4 activity of the metabolite (compound 403) is 5000 nM i.e. inactive compared to the parent compound (PDE4=20 nM).

PO dosing of compound 105-5 mg/kg: Serum Cmax<3 ng/ml of parent compound, however serum Cmaxof the active metabolite compound 106 is 93 ng/ml.

PO dosing of compound 106-5 mg/kg: Serum Cmaxis 133 ng/ml and a bioavailability of 22%.

The invention claimed is:

1. A compound of general formula IIb

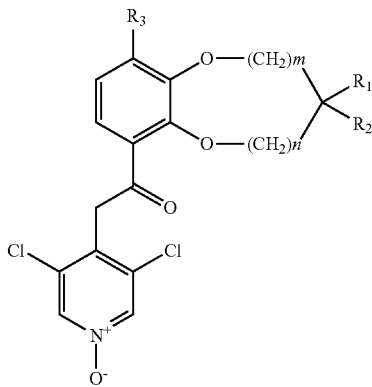

IIb wherein
each of m and n is independently 0 or 1;
$R_1$ and $R_2$, together with the carbon atom to which they are attached, form a heterocyclic ring comprising one or two heteroatoms selected from oxygen, sulfur, —S(O)— and —S(O)$_2$—; and
$R_3$ is —OCHF$_2$, or —OCF$_3$;
or a pharmaceutically acceptable salt, hydrate or solvate thereof.

2. A compound according to claim 1, wherein m and n are both 0.

3. A compound according to claim 1, wherein m and n are both 1.

4. A compound according to claim 1, wherein $R_3$ is —OCHF$_2$.

5. A compound according to claim 1, wherein $R_1$ and $R_2$, together with the carbon atom to which they are attached, form a 4-, 5- or 6-membered heterocyclic ring.

6. A compound according to claim 5, wherein the heterocyclic ring is tetrahydropyran, oxetane, [1,3]dioxolane, [1,3]dioxane, tetrahydrothiopyran, tetrahydrothiopyran-1,1-dioxide, tetrahydrothiopyran-1-oxide, tetrahydrothiophene, [1,3]-dithiane, thietane, [1,3]-dithiane-1,3-dioxide, thietane-1-oxide, or thiethane-1,1-dioxide.

7. A compound according to claim 5, wherein the heterocyclic ring comprises one heteroatom.

8. A compound according to claim 7, wherein the heteroatom is oxygen or —S(O)$_2$.

9. A compound according to claim 1, selected from the group consisting of
2-(3,5-Dichloro-1-oxido-pyridin-4-yl)-1-{9-difluoromethoxy-spiro[2H-1,5-benzodioxepin-3(4H),3' -oxetane]-6-yl}ethanone (compound 102);
2-(3,5-Dichloro-1-oxido-pyridin-4-yl)-1- {9-difluoromethoxy-spiro[2H-1,5-benzodioxepin-3(4H),4'-tetrahydropyran]-6-yl}ethanone (compound 104);
2-(3,5-Dichloro-1-oxido-pyridine-4-yl)-1-(7-difluoromethoxy-2',3',5',6'-tetrahydro-spiro[1,3-benzodioxole-2,4'-(4H)-pyran]-4-yl)ethanone (compound 106); and
2-(3,5-Dichloro-1-oxido-pyridine-4-yl)-1-(7-difluoromethoxy-2',3',5',6'-tetrahydro-spiro[1,3-benzodioxole-2, 4 '-(4H)-thiopyran-1',1 '-dioxide]-4-yl)ethanone (compound 108), or a pharmaceutically acceptable salt, hydrate or solvate thereof.

10. A pharmaceutical composition comprising, as a therapeutically active ingredient, a compound according to claim 1 and a pharmaceutically acceptable carrier or vehicle.

11. A composition according to claim 10, wherein the pharmaceutically acceptable carrier or vehicle is one that is suitable for oral administration.

12. A compound according to claim 1 which is 2-(3,5-Dichloro-1-oxido-pyridin-4-yl)-1-{9-difluoromethoxy-spiro[2H-1,5-benzodioxepin-3(4H),3'-oxetane]-6-yl}ethanone (compound 102), or a pharmaceutically acceptable hydrate or solvate thereof.

13. A compound according to claim 1 which is 2-(3,5-Dichloro-1-oxido-pyridin-4-yl)-1-{9-difluoromethoxy-spiro[2H-1,5-benzodioxepin-3(4H),4 '-tetrahydropyran]-6-yl}ethanone (compound 104), or a pharmaceutically acceptable hydrate or solvate thereof.

14. A compound according to claim 1 which is 2-(3,5-Dichloro-1-oxido-pyridine-4-yl)-1-(7-difluoromethoxy-2',3',5',6'-tetrahydro-spiro[1,3-benzodioxole-2,4'-(4H)-pyran]-4-yl)ethanone (compound 106), or a pharmaceutically acceptable hydrate or solvate thereof.

15. A compound according to claim 1 which is 2-(3,5-Dichloro-1-oxido-pyridine-4-yl)-1-(7-difluoromethoxy-2',3',5',6'-tetrahydro-spiro[1,3-benzodioxole-2, 4'-(4H)-thiopyran-1',1'-dioxide]-4-yl)ethanone (compound 108), or a pharmaceutically acceptable hydrate or solvate thereof.

16. A compound according to claim 1 which is 2-(3,5-Dichloro-1-oxido-pyridin-4-yl)-1-{9-difluoromethoxy-spiro[2H-1,5-benzodioxepin-3(4H),3'-oxetane]-6-yl}ethanone (compound 102).

17. A compound according to claim 1 which is 2-(3,5-Dichloro-1-oxido-pyridin-4-yl)-1-{9-difluoromethoxy-spiro[2H-1,5-benzodioxepin-3(4H),4'-tetrahydropyran]-6-yl}ethanone (compound 104).

18. A compound according to claim 1 which is 2-(3,5-Dichloro-1-oxido-pyridine-4-yl)-1-(7-difluoromethoxy-2', 3',5',6'tetrahydro-spiro[1,3-benzodioxole-2,4'-(4H)-pyran]-4-yl)ethanone (compound 106).

19. A compound according to claim 1 which is 2-(3,5-Dichloro-1-oxido-pyridine-4-yl)-1-(7-difluoromethoxy-2', 3',5',6'-tetrahydro-spiro[1,3-benzodioxole-2, 4'-(4H)-thiopyran-1',1'-dioxide]-4-yl)ethanone (compound 108).

20. A compound according to claim 1 which is 2-(3,5-Dichloro-1-oxido-pyridin-4-yl)-1-{9-difluoromethoxy-spiro[2H-1,5-benzodioxepin-3(4H),3'-oxetane]-6-yl}ethanone (compound 102), or a pharmaceutically acceptable hydrate thereof.

21. A compound according to claim 1 which is 2-(3,5-Dichloro-1-oxido-pyridin-4-yl)-1-{9-difluoromethoxyspiro[2H-1,5-benzodioxepin-3(4H),4'-tetrahydropyran]-6-yl}ethanone (compound 104), or a pharmaceutically acceptable hydrate thereof.

22. A compound according to claim 1 which is 2-(3,5-Dichloro-1-oxido-pyridine-4-yl)-1-(7-difluoromethoxy-2',3',5',6'-tetrahydro-spiro[1,3-benzodioxole-2,4'-(4H)-pyran]-4-yl)ethanone (compound 106), or a pharmaceutically acceptable hydrate thereof.

23. A compound according to claim 1 which is 2-(3,5-Dichloro-1-oxido-pyridine-4-yl)-1-(7-difluoromethoxy-2',3',5',6'-tetrahydro-spiro[1,3-benzodioxole-2, 4'-(4H)-thiopyran-1',1'-dioxide]-4-yl)ethanone (compound 108), or a pharmaceutically acceptable hydrate thereof.

24. A compound according to claim 1 which is 2-(3,5-Dichloro-1-oxido-pyridin-4-yl)-1-{9-difluoromethoxy-spiro[2H-1,5-benzodioxepin-3(4H),3'-oxetane]-6-yl}ethanone (compound 102), or a pharmaceutically acceptable solvate thereof.

25. A compound according to claim 1 which is 2-(3,5-Dichloro-1-oxido-pyridin-4-yl)-1-{9-difluoromethoxy-spiro[2H-1,5-benzodioxepin-3(4H),4'-tetrahydropyran]-6-yl}ethanone (compound 104), or a pharmaceutically acceptable solvate thereof.

26. A compound according to claim 1 which is 2-(3,5-Dichloro-1-oxido-pyridine-4-yl)-1-(7-difluoromethoxy-2',3',5',6'-tetrahydro-spiro[1,3-benzodioxole-2,4'-(4H)-pyran]-4-yl)ethanone (compound 106), or a pharmaceutically acceptable solvate thereof.

27. A compound according to claim 1 which is 2-(3,5-Dichloro-1-oxido-pyridine-4-yl)-1-(7-difluoromethoxy-2',3',5',6'-tetrahydro-spiro[1,3-benzodioxole-2, 4'-(4H)-thiopyran-1',1'-dioxide]-4-yl)ethanone (compound 108), or a pharmaceutically acceptable solvate thereof.

28. A pharmaceutical composition comprising, as a therapeutically active ingredient, a compound according to claim 12 and a pharmaceutically acceptable carrier or vehicle.

29. A pharmaceutical composition comprising, as a therapeutically active ingredient, a compound according to claim 13 and a pharmaceutically acceptable carrier or vehicle.

30. A pharmaceutical composition comprising, as a therapeutically active ingredient, a compound according to claim 14 and a pharmaceutically acceptable carrier or vehicle.

31. A pharmaceutical composition comprising, as a therapeutically active ingredient, a compound according to claim 15 and a pharmaceutically acceptable carrier or vehicle.

32. A composition according to claim 28, wherein the pharmaceutically acceptable carrier or vehicle is one that is suitable for oral administration.

33. A composition according to claim 29, wherein the pharmaceutically acceptable carrier or vehicle is one that is suitable for oral administration.

34. A composition according to claim 30, wherein the pharmaceutically acceptable carrier or vehicle is one that is suitable for oral administration.

35. A composition according to claim 31, wherein the pharmaceutically acceptable carrier or vehicle is one that is suitable for oral administration.

* * * * *